(12) United States Patent
Staffler et al.

(10) Patent No.: US 9,625,459 B2
(45) Date of Patent: Apr. 18, 2017

(54) METHOD FOR DIAGNOSING ALZHEIMER'S DISEASE (AD)

(71) Applicant: AFFIRIS AG, Vienna (AT)

(72) Inventors: Guenther Staffler, Vienna (AT); Andreas Mairhofer, Vienna (AT); Achim Schneeberger, Vienna (AT); Martina Lutterova, Bratislava (SK); Walter Schmidt, Vienna (AT); Frank Mattner, Vienna (AT)

(73) Assignee: AFFIRIS AG, Vienna (AT)

( * ) Notice: Subject to any disclaimer, the term of this patent is extended or adjusted under 35 U.S.C. 154(b) by 0 days.

(21) Appl. No.: 14/346,910

(22) PCT Filed: Sep. 20, 2012

(86) PCT No.: PCT/EP2012/068493
§ 371 (c)(1),
(2) Date: Mar. 24, 2014

(87) PCT Pub. No.: WO2013/050248
PCT Pub. Date: Apr. 11, 2013

(65) Prior Publication Data
US 2014/0242727 A1     Aug. 28, 2014

(30) Foreign Application Priority Data

Oct. 4, 2011 (EP) .................................. 11183842

(51) Int. Cl.
*A61K 39/00* (2006.01)
*A61K 38/10* (2006.01)
(Continued)

(52) U.S. Cl.
CPC ......... *G01N 33/566* (2013.01); *G01N 33/564* (2013.01); *G01N 33/6896* (2013.01);
(Continued)

(58) Field of Classification Search
None
See application file for complete search history.

(56) References Cited

U.S. PATENT DOCUMENTS

2007/0166311 A1* 7/2007 Greferath et al. ......... 424/146.1
2009/0104629 A1* 4/2009 Fiala .................. G01N 33/5035
435/7.8

FOREIGN PATENT DOCUMENTS

CN      1371416 A     9/2002
CN      1377278 A    10/2002
(Continued)

OTHER PUBLICATIONS

Britschgi et al., Neuroprotective natural antibodies to assemblies of amyloidogenic peptides decrease with normal aging and advancing Alzheimer's disease. PNAS I| Jul. 21, 2009 | vol. 106 | No. 29 112145-12150.*
(Continued)

*Primary Examiner* — Jeffrey Stucker
*Assistant Examiner* — Aurora M Fontainhas
(74) *Attorney, Agent, or Firm* — Oblon, McClelland, Maier & Neustadt, L.L.P.

(57) ABSTRACT

Disclosed is a method for diagnosing Alzheimer's disease (AD) wherein Aβ-specific antibodies in a biological sample of a person that is suspected of having AD are detected comprising the following steps: —contacting the sample with Aβ-aggregates or with particles having Aβ-aggregate like surfaces and allowing the Aβ-specific antibodies to bind to the Aβ-aggregates, and —detecting the Aβ-specific antibodies bound to the Aβ-aggregates by a single particle detection technique, preferably by fluorescence activated cell sorting (FACS); and wherein the amount of Aβ-specific antibodies detected is compared with the amount in a sample of known AD status.

18 Claims, 9 Drawing Sheets

(51) Int. Cl.
  *C07K 2/00* (2006.01)
  *G01N 33/566* (2006.01)
  *G01N 33/564* (2006.01)
  *G01N 33/68* (2006.01)
(52) U.S. Cl.
  CPC ............... *G01N 2333/4709* (2013.01); *G01N 2800/2821* (2013.01)

(56) References Cited

FOREIGN PATENT DOCUMENTS

| | | |
|---|---|---|
| CN | 101218248 | 7/2008 |
| CN | 101262863 A | 9/2008 |
| EP | 0391714 A2 | 10/1990 |
| WO | 96/12544 A1 | 5/1996 |
| WO | 96/15452 A1 | 5/1996 |
| WO | 2004/074837 A1 | 9/2004 |
| WO | 2010/099199 | 9/2010 |
| WO | 2010 128139 | 11/2010 |
| WO | 2011 106732 | 9/2011 |

OTHER PUBLICATIONS

Gustaw et al., Antigen-antibody dissociation in alzheimer's disease: a novel approach to diagnosis. Journal of Neurochemistry | 2008 | 106 | 1350-1356.*

Funke et al., Single particle detection of Abeta aggregates associated with Alzheimer's disease. Biochemical and Biophysical Research Communications 364 (2007) 902-907.*

Britschgi et al., Neuroprotective natural antibodies to assemblies of amyloidogenic peptides decrease with normal aging and advancing Alzheimer's disease. PNAS | Jul. 21, 2009 | vol. 106 | No. 29 I S1-10 (Supporting Information).*

Zameer et al., Anti-oligomeric Aβ Single-chain Variable Domain Antibody Blocks Aβ-induced Toxicity Against Human Neuroblastoma Cells. J. Mol. Biol. (2008) 384, 917-928.*

Bateman et al., Requirement of aggregation propensity of Alzheimer amyloid peptides for neuronal cell surface binding. BMC Neuroscience 2007, 8:29, 1-13.*

Jan et al., Preparation and characterization of toxic Aβ aggregates for structural and functional studies in Alzheimer's disease research. Nature Protocols 5, —1186-1209 (2010).*

U.S. Appl. No. 14/348,788, filed Mar. 31, 2014, Staffler, et al.

Dubois, et al., "Revising the definition of Alzheimer's disease: a new lexicon", Lancet Neurology, vol. 9, pp. 1118-1127, (Nov. 2010).

McKhann et al., "The diagnosis of dementia due to Alzheimer's disease: Recommendations from the National Institute on Aging-Alzheimer's Association workgroups on diagnostic guidelines for Alzheimer's disease ", Alzheimer's & Dementia, vol. 7, pp. 263-269, (2011).

Hampel, et al., "Biomarkers for Alzheimer's disease: academic, industry and regulatory perspectives", Nature Reviews, Drug Discovery, vol. 9, pp. 560-574, (Jul. 2010).

O'Nuallain, et al., "Anti-amyloidogenic Activity of IgGs Contained in Normal Plasma", J Clin Immunol , vol. 30 (Suppl 1): S37-S42, (2010).

Marcello, et al., "Circulating immune complexes of Aβ and IgM in plasma of patients with Alzheimer's disease", J Neural Transm, vol. 116, pp. 913-920, (2009).

Brettschneider, et al., Decreased Serum Amyloid $\beta_{1-42}$ Autoantibody Levels in Alzheimer's Disease , Determined by a Newly Developed Immuno-Precipitation Assay with Radiolabeled Amyloid $\beta_{1-42}$ Peptide, Biol Psychiatry, vol. 57, pp. 813-816, (2005).

Funke, et al., "Detection of Amyloid —β Aggregates in Body Fluids: A Suitable Method for Early Diagnosis of Alzheimer's Disease?", Current Alzheimer Research , vol. 6, pp. 285-289, (2009).

Maetzler, et al., "Autoantibodies Against Amyloid and Glial-Derived Antigens are Increased in Serum and Cerebrospinal Fluid of Lewy Body-Associated Dementias", Journal of Alzheimer's Disease, vol. 26, pp. 171-179, (2011).

Funke, et al., "Single-Particle Detection Systems for Aβ Aggregates: Adaptation of Surface-Fluorescence Intensity Distribution Analysis to Laser Scanning Microscopy", Rejuvenation Research, vol. 13, No. 2-3, pp. 206-209, (2010), XP002664692.

Fukumoto, et al., "High-molecular-weight β-amyloid oligomers are elevated in cerebrospinal fluid of Alzheimer patients", The FASEB Journal . Research Communication, vol. 1, No. 24, pp. 2716-2726, (2010), XP002664693.

Binder , et al., Autoantibody detection using multiplex Technologies, Lupus, vol. 15, pp. 412-421, (2006).

Janes, et al., "Next-generation flow cytometry", Nature Biotechnology, vol. 29, No. 7, pp. 602-604, (Jul. 2011).

Cannon, et al., "Kinetic analysis of beta-amyloid fibril elongation", Analytical Biochemistry, vol. 328, pp. 67-75, (2004).

Missailidis, et al., "Characterization of Antibody-Antigen Interactions by Fluorescence Spectroscopy", Methods in Molecular Biology, vol. 248, pp. 431-441, (2003).

International Search Report Issued Dec. 10, 2012 in PCT/EP12/068493 Filed Sep. 20, 2012.

European Search Report Issued Dec. 13, 2011 in EP 11 18 3842.1 Filed Oct. 4, 2011.

Written Opinion of the International Searching Authority Issued Dec. 10, 2012, in PCT/EP12/068493 Filed Dec. 10, 2012.

Hiroaki Fukumoto, et al., "High-molecular-weight β-amyloid oligomers are elevated in cerebrospinal fluid of Alzheimer patients", The FASEB Journal, vol. 24, Aug. 2010, pp. 2716-2726.

Written Opinion issued Oct. 10, 2014 in Singaporean Patent Application No. 11201400223S.

Robert D. Moir, et al., "Autoantibodies to Redox-modified Oligomeric Aβ are Attenuated in the Plasma of Alzheimer's Disease Patients", The Journal of Biological Chemistry, vol. 280, No. 17, Issue of Apr. 29, 2005, pp. 17458-17463.

Office Action issued on Jul. 20, 2015, in corresponding application No. 201280049131.8.

Partial Examination Report as received in the corresponding European Patent Application No. 12 761 989.8-1412 dated Sep. 7, 2016.

* cited by examiner

METHOD FOR DIAGNOSING ALZHEIMER'S DISEASE (AD)

This application is a National Stage of PCT/EP12/068493 filed Sep. 20, 2012 and claims the benefit of EP 11183842.1 filed Oct. 4, 2011.

The present invention relates to methods for detecting Aβ-specific antibodies in biological samples, especially in connection with and for diagnosing of Alzheimer's disease (AD).

AD is a complex progressive disorder that involves interacting pathological cascades, including amyloid-β aggregation and plaque formation in the brain, hyperphosphorylation of tau protein with formation of intraneuronal tangles. Concomitant to the aggregation and the hyperphosphorylation of these cerebral proteins inflammatory processes contribute to the loss of the synaptic integrity and progressive neurodegeneration.

The conversion of amyloid β peptide (Aβ or A-beta) from a soluble form with mainly alpha-helical or random coil secondary structure to an aggregated form with beta-sheet secondary structure, that finally forms amyloid plaques in the brain, represents one of the first hallmarks of AD pathology. Several forms of Aβ, C- as well as N-terminally truncated or modified peptides, contribute to Aβ plaque formation in the brain. The three major C-terminal variants of Aβ include the peptides Aβ1-40 (consisting of 40 amino acids (aa) with Val-40 as last aa), Aβ1-42, and Aβ1-43. Beside these major forms of C-terminal truncated peptides also other truncated forms exist that appear less frequently, namely Aβ1-37, Aβ1-38, and Aβ1-39. The N-terminal variants of Aβconsist of Aβ3-40/42/43 and Aβ11-40/42/43. In all these N-terminal truncated forms the glutamic acid holds the first position. This aa is not stable but rather undergoes a change to build the pyroglutamate (pE) resulting in the formation of Aβp(E)3-40/42 and Aβp(E)11-40/42. pE residues are either formed spontaneously or enzymatically by enzymes known as glutaminyl cyclases.

Until recently, the diagnosis of AD was a purely clinical one based on the gradual occurrence of cognitive deficits in at least two domains (e.g., cognition, function), negatively affecting the patient's everyday life without another discernable cause (e.g., vascular). The limitation of clinical diagnosis of AD were high rates of misdiagnoses (diagnostic specificity of 80% by experts) and the fact that the diagnosis could only be made at a late time point when the disease had caused substantial neuronal loss that resulted in functional deficits.

Based on knowledge gathered through the last two decades, the way of diagnosing AD is rapidly changing. A group of researchers led by B. Dubois, Paris, were the first to integrate data, which had emerged from investigations into the pathology underlying AD, into the diagnostic algorithm (Dubois et al., Lancet Neurol. 9 (2010): 1118-1127). According to the authors, the diagnosis of AD is based on a specific cognitive deficit (an alteration of the episodic memory) which has to occur in combination with a change in disease-specific biomarkers (hippocampal atrophy as assessed by structural MRI; AD-typical cerebrospinal fluid signature (low A42, high total tau, high phosphoTau); positive amyloid imaging; defined genetic risk). Recently, this pathophysiology driven diagnostic algorithm has been largely adopted by the NIH-NINCDS working group (McKhann et al., Alzheimer's & Dementia 7 (2011): 263-269). For mainly practical purposes, the NIH NINCDS working group kept the diagnosis of MCI (mild cognitive impairment) of the AD-type as an early stage of AD.

The concept of enhancing the clinical diagnosis of AD by means of biomarker reflecting the pathology of the disease has been adopted by a working group installed by the National Institute of Aging (NIA, NIH, USA) and the Alzheimer Association. By doing so, AD is not any more a diagnosis by exclusion but begins to be a positive one. The fact that NIA and AA did not completely follow the biomarker-driven algorithm proposed by Dubois and colleagues reflects the limitations of the currently available biomarkers. The AD cerebrospinal fluid (CSF) signature may be discussed as an example. The CSF of AD patients shows a typical pattern, namely reduction of Aβ1-42 and elevation of total Tau (tTau) and phosphoTau (pTau). The signature is present in AD patients but does not detect a change over time. In fact, in a population of patients at risk for AD (i.e., MCI patients) it identifies the ones who move on to develop the clinical symptoms. Already at that stage, the CSF shows the same expression pattern and amount of change as in patients with full-blown AD. Thus, while it is not possible to define a normal range for Aβ1-42, tTau and pTau, there is no definition of turning points, i.e. the moment in a given patient when for example the Aβ physiology switches from normal to pathological. The very same is true for any of the currently followed and not yet validated biomarkers. The main reason for this is that there are only a few longitudinal studies assessing this issue because it is not easily possible to repeat CSF-, MRI-, amyloid-imaging examinations because of the risk they impose onto patients and/or the costs associated with them.

Thus, there is still a lack of a reliable biomarker that can be applied repetitively, at low risk and costs. This is especially true since all efforts taken so far to develop blood-based AD biomarkers failed (Hampel et al., Nat. Rev. Drug Discov. 9 (2010): 560-574). The availability of such a biomarker would be of outmost importance for the development of disease-modifying therapies. The earlier such therapies would be administered, the bigger the chances for success. And, one could limit such efforts to true AD cases identified with the help of a specific biomarker.

Thus far, Aβ (various Aβ species and aggregation states tested) have been evaluated in AD and MCI, the pre-dementia stage of AD. Recent findings show that there is an anti-amyloidogenic-activity of IgG and IgM contained in plasma and cerebrospinal fluid of AD patients and healthy controls (O'Nuallain et al., J. Clin. Immunol. 30 (2010) Suppl. 1: S37-S42; Marcello et al., J Neural. Transm. 116 (2009): 913-920). Results obtained by ELISA or immuno-precipitation assays assessing IgG and/or IgM specific for various Aβ forms/aggregation states showed that AD- and MCI patients exhibit lower levels of serum Aβ auto-antibodies than healthy controls. Although these studies showed a difference in auto-antibody concentration, the used methods lack the sensitivity and specificity that would be necessary to use them as predictive diagnostic tool to identify AD- or MCI patients with high selectivity and specificity. Most of the methods used so far are based on ELISA technology. To increase the sensitivity in these assays some approaches use radioactive labelling of the Aβ1-42 peptide. The ROC (receiver operating characteristic) analysis of Brettschneider et al., (Brettschneider et al., Biol. Psychiatry 57 (2005): 813-817), reached a specificity of 46.7% when sensitivity was set at 81.3% using an immunoprecipitation assay with chloramine T labelled Aβ1-42 to measure the difference between healthy controls and AD patients. In contrast Bayer et al. (WO 2010/128139 A1; Marcello et al., J Neural. Transm. 116 (2009): 913-920) used an ELISA based method where a pyroglutamate-Aβ fragment was coated on the plate. In this case, the detection of anti-Aβ specific IgM-autoantibodies in healthy controls and AD patients with an anti-IgM-HRP antibody showed that specificity was 60% when sensitivity was set to 80%. So far, none of these methods fulfilled the criteria that would qualify them as predictive biomarker (>80% specificity) for AD.

Not known is the reason for the reduced serum concentration of Aβ-specific antibodies in these two groups of patients. There are two general and non-mutually exclusive explanations: reduced production (disease-specific versus general immunosenescence) and redistribution (antibodies are trapped in amyloid deposits present for example in the brain). Support for a potential function of these Aβ-specific (auto)antibodies comes from recent studies demonstrating that commercially available blood products, namely the pooled IgG fraction extracted from plasma derived from healthy donors, has been shown to contain antibodies specific for Aβ peptides. Two such products, intravenous immunoglobulin (IVIG) preparations of two different companies, are currently undergoing clinical testing to evaluate their potential to interfere with or prevent AD pathology.

Another unanswered question is whether the level of Aβ-specific antibodies is reduced in disease entities with an Aβ component in their pathophysiology, namely Parkinson's dementia (PDD), Dementia with Lewy Bodies (DLB), Cerebral Amyloid Angiopathy (CAA), chronic head trauma (e.g., boxing). Investigation of the level of Aβ-aggregate-specific antibodies in these diseases could add to the present understanding of the processes that result in the reduction of the serum concentration of Aβ-aggregate-specific antibodies in AD. Investigation of sera of patients with these diseases could clarify the question as to whether AD results from a specific immunodeficiency (in the case where Aβ-specific antibody titers are only reduced in AD but not in other diseases characterized by Aβ pathology) or whether the reduced levels of Aβ-specific antibodies result from redistribution due to extensive Aβ pathology. In the former case, the test would be a highly disease-specific biomarker and, as a result, should be helpful in differentiating AD from the aforementioned disease entities. Assuming the second scenario, the test could qualify for the identification of patients whose disease is driven by Aβ pathology.

In WO 2010/128139 A1, biomarkers and methods for diagnosing AD are disclosed, especially antibodies against pGlu Aβ. Funke et al. (Curr. Alz. Res., 6 (3) (2009): 285-289) discussed whether the detection of Aβ aggregates in body fluids is a suitable method for early diagnosis of AD. Maetzler et al. (J. Alz. Dis. (1) (2011): 171-179) reported that autoantibodies against amyloid and glial-derived antigens are increased in serum and cerebrospinal fluid of Lewy body-associated dementias. Funke et al. (Rejuv. Res. 13 (2-3) (2010): 206-209) disclosed a single-particle detection system for Aβ aggregates. Fukumoto et al. (Faseb J., 1 (24) (2010): 2716-2726) disclosed that high-molecular weight β-amyloid oligomers are elevated in cerebrospinal fluid of AD patients.

It is an object of the present invention to provide means for improving the diagnosis of AD, especially for tracking early stages of the disease and for observing the development of clinical trials for drugs for the treatment of AD. It is a further object to provide reliable tools for detecting anti-Aβ antibodies in biological samples, especially in samples of human AD patients or human individuals who are suspected to have or are at risk of developing AD.

Therefore, the present invention provides a method for diagnosing Alzheimer's disease (AD) wherein Aβ-specific antibodies in a biological sample of a person that is suspected of having AD are detected comprising the following steps:

contacting the sample with Aβ-aggregates or with particles having Aβ-aggregate like surfaces and allowing the Aβ-specific antibodies to bind to the Aβ-aggregates, and detecting the Aβ-specific antibodies bound to the Aβ-aggregates by a single particle detection technique, preferably by fluorescence activated cell sorting (FACS);

and wherein the amount of Aβ-specific antibodies detected is compared with the amount in a sample of known AD status.

With the present invention, a new method to detect Aβ-specific auto-antibodies is disclosed for use as diagnostic tool which is extremely helpful in diagnosing AD and monitoring the development of AD. The present method is based on the invention that not just single Aβ peptides are used as capturing tools for the Aβ-specific antibodies, but that instead Aβ-aggregates are used and that thereby generated antibody-Aβ-aggregate complexes are detected using a single particle detection technique and that the amount of such antibodies correlate with the development of AD. The lower the amount is that is detected by the present method, the more advanced the disease status is with respect to AD. Briefly, Aβ-aggregates (derived from different Aβ truncated and modified versions) are generated e.g. by overnight incubation. Subsequently, Aβ-aggregates are incubated with serum samples derived either from healthy donors (HD) or from AD patients to allow binding of present antibodies (both IgG and IgM). Antibodies bound to Aβ-aggregates can be detected by any suitable method available to a person skilled in the art, e.g. by using a labelled secondary antibody which recognises the Aβ-specific antibody bound to the Aβ-aggregates. For example a phycoerythrin (PE)-labelled secondary antibody can be used. Thereafter, the immune complexes comprising the Aβ-specific antibody bound to the Aβ-aggregates (and optionally one or more detection agents, such as secondary antibodies) are measured using a single particle detection technique, such as FACS (fluorescence activated cell sorting)-analysis also known as flow cytometry. Using the method according to the present invention, it could be shown that AD patients contain less Aβ-specific immunoglobulins which are reactive towards the Aβ-aggregates (free Aβ-specific immunoglobulins) provided according to the present invention compared to healthy subjects. Furthermore, using the method according to the present invention, it could be shown that reactivity of Aβ-specific immunoglobulins (towards the Aβ-aggregates provided according to the present invention) derived from AD patients can be increased by a procedure known as demasking (removing of potentially bound Aβ-antigens from autoantibodies). This is in contrast to the reactivity of Aβ-specific immunoglobulins from healthy subjects where such an increase of reactivity towards the Aβ-aggregates cannot be detected after treating these sera in a special way. On the other hand, the reactivity of IgM-antibodies after demasking (=dissociation of already bound Aβ in the serum) revealed an increased level of IgM in AD patients. Additionally, also the difference between IgG levels with and without demasking was determined (delta (Δ) values). This parameter was also elevated in AD patients as compared to healthy controls showing higher antibody occupancy by Aβ of antibodies in the pathological state of the disease. Furthermore, with the present invention data are provided showing that the present method has a much higher capacity to detect Aβ-specific antibodies and thus has a much higher power to diagnose AD compared to methods published so far. Given these facts, the method according to the present invention fulfils the theoretical prerequisites of a predictive diagnostic tool to identify AD and to follow the clinical response of a given patient to treatment.

The present invention was developed for the analysis of Aβ-specific antibodies in human samples. It is therefore a preferred embodiment to detect human Aβ-specific antibodies, preferably human IgG or IgM antibodies, especially human IgG antibodies. As already mentioned, the detection of Aβ-specific antibodies in human is known in principle in the art; however, the role as a possible biomarker could not be verified. As shown with the present invention, this was also due to the analytical insufficiency of the detection methods available in the art. Due to the superiority of the method according to the present invention, the availability of these antibodies in human samples as biomarkers is enabled. The present method is therefore specifically suited to detect autoantibodies in biological samples. Accordingly, in a preferred embodiment of the present method, the Aβ-specific antibodies to be detected and quantified are autoantibodies.

In contrast to prior art methods, the present method uses Aβ-aggregates as probe for binding the Aβ-specific antibodies from the samples. Although such aggregates are known in principle in the art, it was not realised that the use of such aggregates in the analysis of Aβ-specific antibodies, especially in human samples, could significantly improve such methods, also in combination with the single particles detection techniques, such as FACS. Due to the use of such aggregates, the detection with single particles detection techniques (which are established techniques in various different fields and for different questions) is possible for analysing Aβ-specific antibodies in human samples (such as blood) which are usually very complex and difficult to handle.

Preferably, the dimensions of the aggregates to be used according to the present invention are standardised for analytical use. This can be done by establishing certain parameters during production of the aggregates. Depending on the conditions applied during generation of the aggregates, the size of the aggregates can be adjusted. Preferred sizes of the Aβ-aggregates according to the present invention are from 50 nm to 15 µm, preferably from 100 nm to 10 µm, especially from 200 nm to 5 µm (defined by the length of the aggregates (i.e. the longest ex-tension).

A preferred method to provide aggregates suitable for the present invention comprises the step of incubating Aβ-1-42 peptides, Aβ-1-43 peptides, Aβ-3-42 or Aβ-p(E)3-42 peptides or less preferably to Aβ-peptides that are truncated at the C-terminus such as Aβ-1-40 peptide, at a pH of 2 to 9 for at least 20 min, preferably at least 1 h, especially at least 4 h. The duration of incubation is one of the parameters to adjust the size of the aggregates: the longer the incubation, the larger are the aggregates. Typical incubation times are from 10 min to 24 h. Shorter incubation times usually result in only very short aggregates and low number of aggregates; the aggregates produced with significantly longer incubation times than 48 h are usually not preferred in the present method. Of course, aggregates may also be sorted and "sieved" to arrive at the desired size, if needed, e.g. by fractionated centrifugation and similar techniques.

According to the present method, the samples wherein the Aβ-specific antibodies are to be detected are contacted with the Aβ-aggregates to achieve binding of the Aβ-specific antibodies possibly present (and reactive vis-a-vis Aβ-aggregates) in the samples. The concentration of the Aβ-aggregates has therefore to be adjusted in order to provide enough binding positions for the antibodies. Accordingly, the concentration of the Aβ-aggregates for binding the antibodies in the sample is preferably in the range of 0.001 to 1 µM, preferably 0.01 to 0.1 µM. The optimal concentration is also dependent on the nature of antibodies to be bound, the nature of the sample, the planned contact time and the size of the aggregates.

The present method is mainly aimed for application on human samples. It is therefore preferred that biological sample is human blood or a sample derived from human blood, preferably human serum or human plasma; human cerebrospinal fluid or human lymph. With such sample sources, also serial and routine testing may be established (especially for samples derived from blood).

Preferred contact times which allow proper binding of the antibodies in the sample to the aggregates are at least 10 min (e.g. 10 min to 48 h), preferably from 15 min to 24 h, especially from 30 min to 2 h.

If the biological sample is not specifically pre-treated, the Aβ-specific antibodies which have a binding capacity to the Aβ-aggregates will be bound during contact with the Aβ-aggregates. The Aβ-specific antibodies which are masked in the sample (i.e. those antibodies which are already bound to a binding partner (e.g. an Aβ-comprising structure, or endogenous Aβ peptides)) will not be detected by the method according to the present invention (absent such specific sample pre-treatment). Whereas the identification and quantification of only reactive antibodies will in many cases be sufficient and desired, there may be situations or diagnostical questions where the total amount of Aβ-specific antibodies in the sample should be detected (reactive and unreactive) or all, the number of reactive Aβ-specific antibodies, the unreactive ("masked") and the total number of Aβ-specific antibodies.

Therefore, according to another preferred embodiment of the present invention, the samples are demasked, i.e. the Aβ-specific antibodies are "freed" from any binding to binding partners present in the sample previous to the contact with the Aβ-aggregates according to the present invention. This allows detection of all Aβ-specific antibodies in the sample and not only detection of those antibodies which are not bound to a binding partner in the sample ("free" or "reactive" antibodies). In the course of the present invention it was determined that the amount of reactive Aβ-specific antibodies, especially reactive Aβ-specific IgG, was a key marker for the diagnosis and development of AD. The present method is, as stated above, also suitable for determining the overall amount of Aβ-specific antibodies in a sample, i.e. the free (or "reactive") antibodies as well as those antibodies which are already bound (e.g. to Aβ structures) in the sample. This can be helpful in establishing the difference (Δ) of reactive vs. non-reactive antibodies in a sample, a parameter which is also of significant importance for AD diagnosis. Whereas such difference is not present (or low) in persons with "healthy status" concerning AD, this difference is crucial for the marker function in AD, concerning both Aβ- specific IgG and Aβ-specific IgM. In order to use Aβ-specific IgM as parameter for AD diagnosis, a demasking step prior to performance of the present method is in particular preferred, thus the difference (Δ) of reactive vs. non-reactive antibodies in the sample will be defined and used as relevant parameter.

The method according to the present invention applies a single particle detection technique. Such techniques allow identifying and quantifying ("count") the number and amount of "positive" binding results of the Aβ-specific antibody to the Aβ-aggregates. A preferred embodiment of this technology is FACS which is an established technique in the present field. Other detection methods to be used to detect the antibodies bound to the Aβ-aggregates are e.g. Luminex or mass cytometry.

According to the Luminex technology, sample preparation may be performed as described in Material and Methods. Following sample preparation Aβ-aggregates recognized by specific Aβ-specific antibodies may be detected by a secondary antibody coupled to fluorescent-dyed microspheres which can be detected in multiplex detecting systems e.g. a Luminex reader (Binder et al., Lupus 15 (2005): 412-421).

If mass cytometry is used as single particle detection technique, sample preparation may also be performed as described in Material and Methods of the example section below. Sample preparation is done as described. Following sample preparation Aβ-aggregates recognized by specific Abs may be detected by a secondary antibody coupled to stable isotopes of transition elements which can be detection by atomic mass spectrometry. The sample can then be sprayed through an argon plasma filled inductive coil heated to a temperature of >5,500 K. The sample is vaporized and ionized into its atomic constituents, and the number of the isotope-tagged antibody is quantified by time-of-flight mass spectrometry (Janes et al., Nat. Biotechnol. 29 (2011): 602-604).

Alternatively it is also possible to apply single particle detection techniques where one binding partner (Aβ-aggregates or antibody/serum) are immobilized but binding is measured under flow conditions. Examples are the Hybcell technology and the Surface Plasmon Resonance technology. Using the Hybcell technology in the present invention, serum samples can be spotted on the surface of the Hybcell (a rotating cylinder) and incubation can be performed with directly fluorescence-labelled preincubated Aβ-aggregates or alternatively with a fluorescence-labelled monoclonal Aβ-specific second antibody. Antibodies bound to Aβ-aggregates are detected with a laser (Ronacher, Anagnostics Technical Note ANA-TN-005 (2010)). If Surface Plasmon Resonance is used in the method according to the present invention, a reverse setup can be applied: the preincubated Aβ-aggregates can be immobilized on a chip surface. The binding of Aβ-specific antibodies from serum to the Aβ-aggregates on the chip can be detected by increase of mass on the chip surface and therefore no labelling of the binding partners is necessary. To increase sensitivity or determine IgG-subtypes a serial injection of anti-IgG-AB is possible (Cannon et al., Anal. Biochem. 328 (2004): 67-75). Instead of directly immobilizing Aβ-aggregates to the chip surface a capture antibody can be used. For this setup an Aβ-specific antibody is immobilized on the chip surface followed by the injection of preincubated Aβ-aggregates. After the capturing of the aggregates serum is injected and reactivity is measured by increase of mass.

Detection of the binding of Aβ-specific antibodies to the Aβ-aggregates according to the present invention can be performed by any suitable method known e.g. Fluorescence Spectroscopy (Missailidis et al., Methods in Molecular Biology 248 (2003): 431-441) for detecting the Aβ-specific antibodies bound to the Aβ-aggregates by a secondary antibody (e.g. a secondary labelled anti-IgG- or anti-IgM-antibody).

Detection of autoantibodies bound to aggregates can also be performed using substrates specifically binding antibodies such as Protein A or Protein G. Another possibility is to precipitate Aβ-aggregate specific autoantibodies using the Aβ-aggregates, wash the complex and biotinylate the antibodies. Subsequently streptavidin can then be used as second step reagent.

According to a preferred embodiment of the present invention, the particles having Aβ-aggregate like surfaces are beads with Aβ-aggregates immobilised on their surface, especially magnetic beads.

The sample of known AD status can be any sample value which allows classifying the sample which is assessed by the method according to the present invention. It may be a real, physical sample of a person with known AD-status (e.g. a healthy person, not having AD or an AD patient, especially an AD patient with a known disease status (e.g. determined by Mini-Mental State examination (MMSE))) or a comparative value, such as calibration curve. A preferred calibration curve includes comparative amounts of Aβ-specific antibodies in the same type of sample (e.g. a blood sample) in an AD status calibration curve, especially a MMSE curve. In a standardised assay system, the absolute amounts of Aβ-specific antibodies detected according to the present invention can be correlated to an AD status. Decreasing amounts of Aβ-specific antibodies for a given patient at different time points indicates progression of the disease.

It is also possible to define certain threshold values of Aβ-specific antibodies in the sample for defined disease status (e.g. "healthy", mild AD, advanced AD, or according to the MMSE scale). The threshold values, of course depend on the sample and on the exact detection system, but may be developed for any standardised way in which the present invention is performed. The Aβ-specific IgG concentration in serum of healthy persons is usually between 1000 and 5000 ng/ml whereas the IgG concentration of AD patients is usually much lower, e.g. in the range of 250 to 1500 ng/ml. Most of AD patients have less than 1000 ng/ml. Therefore, according to a preferred embodiment of the present invention, the detection of an amount of Aβ-specific antibodies in the sample which is lower than a threshold level is indicative of AD, wherein the threshold level is 1500 ng/ml or lower, preferably 1000 ng/ml or lower, especially 750 ng/ml or lower. On the other hand, rise of this IgG concentration in the course of AD treatment, especially AD treatment by immunotherapy indicates successful immunotherapy. For example, if the level rises from under 750 ng/ml to over 1000 ng/ml or even over 1500 ng/ml, this would indicate successful immunotherapy.

Preferably, the detected amount of Aβ-specific antibodies is correlated to a MMSE result of the same person at the same time the sample was taken from the person.

The method according to the present invention is specifically suitable for monitoring a given AD patient with respect to the development of the disease, especially for correlating the diagnostic results according to the present invention with other diagnostic tools for determination of the AD status and/or for monitoring the effectiveness of therapeutic interventions. Accordingly, in a preferred embodiment of the present invention the method is performed at least twice on samples of the same person taken at a different time. Preferably, the detected amounts of Aβ-specific antibodies are correlated to MMSE results of the same person at the same times the samples were taken from the person. For monitoring the development of AD in a given patient, it is preferred to perform the method according to the present invention in regular intervals, e.g. at least once each six months, preferably at least once each three months, especially at least once each month.

The present method is therefore specifically suited for using in connection with AD diagnosis in a monitoring manner over time. With the present invention, Aβ-specific autoantibodies in human patients are provided as markers for AD status. People with "normal" level of Aβ-specific antibodies in their blood are "healthy" with respect to AD. If this level is modified in a patient with AD or subjects with a risk of developing AD or being suspected to have AD, such modification level correlates with AD. A "modified" level may be a modification of the absolute number of the Aβ-specific antibodies or a modification of the reactivity of the totality of the Aβ-specific antibodies (e.g. of a given class of Aβ-specific antibodies (IgG, IgM, etc.). For example, decreased reactive Aβ-specific IgG correlates with and is a marker for AD. On the other hand, with IgM, changes of the level of (non-reactive; i.e. bound or masked) Aβ-specific IgM into the other direction have a marker function with respect to AD. With the present method, when the "healthy" level of reactive Aβ-specific IgG is set to 100%, a significant decrease in reactive Aβ-specific IgG, e.g. a decrease to 70% and lower, to 50% and lower or to 30% and lower, is indicative of development of AD. On the other hand, when the "healthy" level of Aβ-specific IgM is set to 100%, an increase in total IgM (reactive+unreactive) of at least 30%, e.g. at least 50% or at least 100%, in a blood sample indicates development of AD.

Accordingly, a preferred field of use of the present invention is the diagnosis of Alzheimer's disease (AD). However, the present invention is usable for all pathologies connected to or being related to Aβ ("Aβ pathologies"), especially to pathologies where Aβ deposits are occurring in the course of the disease. Examples for such Aβ pathologies are Parkinson's dementia (PDD), Dementia with Lewy Bodies (DLB), Cerebral Amyloid Angiopathy (CAA), Inclusion body myositis (IBM; especially sporadic IBM (sIBM)), or chronic head trauma (e.g., boxing).

Since the present invention provides a marker for AD and even for the development of AD, it is possible to use this method for observing the development of the disease and the performance of possible treatment methods, especially whether the method of treatment enables to establish "healthy" or "healthier" levels of Aβ-specific antibodies, especially IgG or IgM.

The present method is therefore preferably used for the monitoring of AD patients, especially AD patients who are treated with medicaments for curing or ameliorating AD. The present method can be successfully applied for observing patients in clinical trials for AD vaccines (e.g. with AD mimotopes according to WO 2004/062556 A, WO2006/005707 A, WO2009/149486 A and WO 2009/149485 A; or with Aβ-derived vaccines according to WO 99/27944 A) or Aβ-targeting disease-modifying drugs.

The method according to the present invention can also be used for evaluating the risk of developing AD or for detecting early stage AD. With the present invention, it is in principle made possible to detect changes in the immunological set-up of patients with respect to Aβ-specific autoantibodies at a significantly earlier point in time than cognitive impairments. This could allow a significant improvement of early diagnosis of AD with respect to a much larger part of the population if established in routine testing format. This makes patients eligible for early stage treatment regimens and/or prevention (or delay) strategies for AD, especially vaccinations.

According to another aspect, the present invention relates to a kit for performing the method according to the present invention comprising
  Aβ-aggregates, and
  a sample container, especially for human samples (e.g. blood, serum, plasma).

Preferably, the kit according to the present invention may further contain means for detecting Aβ-aggregates being bound to Aβ-specific antibodies, preferably secondary antibodies, especially labelled secondary antibodies, e.g. anti-IgG- or anti-IgM-antibodies). Further components can be standard samples, positive and/or negative controls, instructions for use and suitable packaging means (e.g. stable boxes, coloured vials, etc.).

The present invention is further illustrated by the following examples and the drawing figures, yet without being restricted thereto.

FIG. 3 shows the comparison of assay sensitivity for three different methods. (A) Aβ1-42 aggregates were incubated with a dilution series of IVIG and reactivity was determined in FL-2 channel using flow cytometry. (B) IVIG titration on Maxisorp ELISA plates coated with Aβ1-42 over night at pH9.2. (C) Label free detection of different concentrations of IVIG interacting with mainly biotinylated Aβ1-42 immobilized on SA-Chip using surface plasmon resonance (Bia-Core). Please note that for comparison all results are given in fold-background signal.

FIG. 4 shows the determination of Aβ-specific IgG autoantibody reactivity in indicated serum samples. Control sera from healthy donors (30 to 50 years of age), or sera derived from AD-patients were subjected to the described FACS assay. Fluorescence intensity of Aβ-aggregates was evaluated in FL2-PE channel and is expressed as Median Fluorescence Intensity (MFI).

FIG. 5 shows a ROC curve analysis. IgG specific anti-Aβ1-42 reactivity from sera derived from AD patients with sera derived from healthy donors was compared.

FIG. 7 shows a ROC curve analysis. IgG specific anti-Aβ3-42 reactivity from sera derived from AD patients with sera derived from healthy donors was compared.

FIG. 8 shows a ROC curve analysis. IgG specific anti-Aβp(E)3-42 reactivity from sera derived from AD patients with sera derived from healthy donors was compared.

FIG. 9A shows the determination of Aβ-specific IgM auto-antibody reactivity in indicated serum samples. Control sera from healthy donors, or sera derived from AD-patients were subjected to the described FACS assay. Fluorescence intensity of Aβ-aggregates was evaluated in FL2-PE channel and is expressed as Median Fluorescence Intensity (MFI).

FIG. 9B shows a ROC curve analysis. IgM specific anti-Aβ1-42 reactivity from sera derived from AD patients with sera derived from healthy donors was compared.

FIG. 11 shows a ROC curve analysis. IgM specific anti-Aβ1-42 reactivity from sera derived from AD patients with sera derived from healthy donors was compared after auto-antibody demasking.

FIG. 12 shows a ROC curve analysis. IgG specific anti-Aβ1-42 reactivity of sera derived from AD patients and sera derived from healthy individuals were analyzed before and after antigen dissociation. Delta values were used calculate the ROC curve.

EXAMPLES

Materials and Methods

Detection of Aβ-Specific Antibodies Using Surface Plasmon Resonance (SPR-BIAcore)

The Biacore system offers a variety of chips that can be used for immobilization. For this experiment a streptavidin (SA) coated chip was used. To avoid unspecific binding of the ligand via side chains to the chip surface C-terminally biotinylated Aβpeptides (purchased from Anaspec) were used. Since the biotin-streptavidin complex is extremely stable it is best suitable for extended serial experiments. To optimize the robustness of the chip and therefore the reproducibility, a maximum of response units (~1500 RU) was immobilized onto flow cells whereas flow cell 1 was left empty and used as reference. To avoid unspecific binding on the chip surface, free biotin was used to saturate free SA binding sites on all four flow cells. Human samples (have been diluted 1:10 to 1:100 in HBS pH 7.4) and a dilution series of IVIG ranging from 1 mg/ml to 10 μg/ml was measured (diluted in HBS pH 7.4 as well). The chip surface was regenerated after each sample injection with 10 mM glycin-HCl (pH 1.8). All experiments were performed at 25° C. A standardized protocol was used for injection starting with an association phase of 200 seconds followed by a dissociation phase of 600 seconds. The $R_{max}$ value is defined as the response level (measured in RU) at the end of sample injection. For signal evaluation $R_{max}$ values were determined using the integrated BIA-evaluation software.

Detection of Aβ-Specific Antibodies Using ELISA

Different Aβ peptides (purchased from rPeptide) were diluted in 100 mM $NaHCO_3$ (pH 9.2) at a concentration of 5 μg/ml and coated on Maxisorp 96-well plates overnight. To prevent unspecific binding plates were blocked using 1% BSA/PBS at 37° C. for 1 h. The ELISA was performed with a serial dilution of human sera samples (starting with a dilution of 1:10) or with adding IVIG in concentrations ranging from 1 mg/ml down to 10 μg/ml diluted in binding buffer (PBS/0.1% BSA/0.1% Tween20) at 37° C. for 1 h. After repeated washing steps (3×) with PBS/0.1% Tween20 the secondary anti-human Ig HRP (0.5 μg/ml) detection-antibody was added for 1 h at 37° C. Samples were washed again 3× and ABTS (0.68 mM in 0.1 M citric acid pH 4.3) was added for 30 min for assay development before OD-measurement on plate reader (Biotek—Gen5 Program) at wave length 405 nm.

Detection of Aβ-Specific Antibodies Using FACS Analysis

Prior to analysis, the lyophilized β-amyloid peptides were subjected to a disaggregation procedure. For this purpose lyophilized Aβ species were dissolved in 1% $NH_4OH$ (pH 11). Dissolved Aβ peptides were subsequently aliquoted and stored at −20° C. To induce the formation of aggregates, the different Aβ-species were incubated at a concentration of 20 μM in an aqueous solution (pH 5) at 37° C. on shaker (350 rpm) overnight in an Eppendorf tube. The formation of Aβ-aggregates could be confirmed by Thioflavin T (ThT) staining in FACS (FSC/FL1). Aggregated Aβ-species were diluted to 0.15 μM in sterile filtered 0.5% BSA and pre-incubated for 30 min in a final volume of 95 μl on a 96-well plate. 5 μl of pre-diluted human plasma or Abs (in 0.5% BSA/PBS) was added to 95 μl of Aβ-aggregate-solution. The final dilution of plasma ranged from 1:1000 up to 1:10.000. For monoclonal antibodies, concentrations below 0.5 μg/ml were used. After 45 or 60 min incubation at room temperature (RT) on shaker (350 rpm) 200 μl of 0.5% BSA/PBS was added in every well and centrifuged for 5 min at 3000 rpm (96-well plate-centrifuge). Supernatant was removed and washing step was repeated again with 200 μl of 0.5% BSA/PBS. After the second wash the SN was discarded and pellet was re-suspended in 100 μl 0.5% BSA/PBS containing a 1:1000 dilution of labelled secondary anti-IgG (H+L)-PE or a 1:500 dilution of anti-IgM, Fc5μ antibody (both Jackson Immuno Research). Samples were incubated for another 45 or 60 min at RT on shaker (350 rpm) and measured on FACS Canto equipped with high-throughput sampler (HTS). Aggregates were gated in FSC/SSC and mean respectively median fluorescence intensity (MFI) was measured and evaluated in FL2-PE channel, and reactivity of ThT to Aβ-aggregates was measures and evaluated in FL1-FITC channel, using FACS Diva software.

Demasking

To disrupt the binding of Aβ specific auto-antibodies to Aβ likely present in patient sera and, therefore, preventing detection of these Aβ bound auto-antibodies by antigen-based methods (like ELISA or FACS), sera were pre-diluted in 10 mM Glycin pH2.6 at a dilution of 1:16.7 for 5 min.

To disrupt the potential binding of Aβ antigens to auto-antibodies sera were pre-diluted in 10 mM Glycin pH2.6 at a dilution of 1:16.7 for 5 min. 5 μl of the acidified serum were then co-incubated with 3 μl of Aβ1-42 (100 μg/ml) for another 5 min. Then the mixture was neutralized by addition of 92 μl of 0.5% BSA/PBS and incubated for 20 to 60 min.

Washing steps and incubation with secondary antibody were performed as described above for non-demasked serum.

Results

Aβ-Aggregates: Oligomerization and Fibril Formation

The formation of Aβ-aggregates (including Aβ oligomers, fibrils and fibrillar aggregates) from monomeric Aβ has been intensively investigated under multiple conditions in the recent years. It has been found that aggregation of Aβ peptides is very much dependent on different conditions including pH, temperature, buffer composition and protein concentration. Aggregation starts with the formation of β-hairpins from monomers leading to soluble oligomers. Conformational transition into parallel β-sheets then leads to the formation of fibrils and fibrillar aggregates, which can be precipitated by centrifugation. Recent findings have shown that Aβ40 and Aβ42 aggregates produced at pH 7.4 comprise fibrils with a 5 nm wide filament with a slight tendency to laterally associate into bundles (into 15 to 25 nm wide filaments). The length of such a single fibril lies in the range of sub-micrometer (50-100 nm) up to 10-15 μm as determined by transmission electron microscopy. One characteristic of these Aβ fibrils is that they specifically intercalate with a fluorescent dye, the Thioflavin T (ThT).

Figure 1:
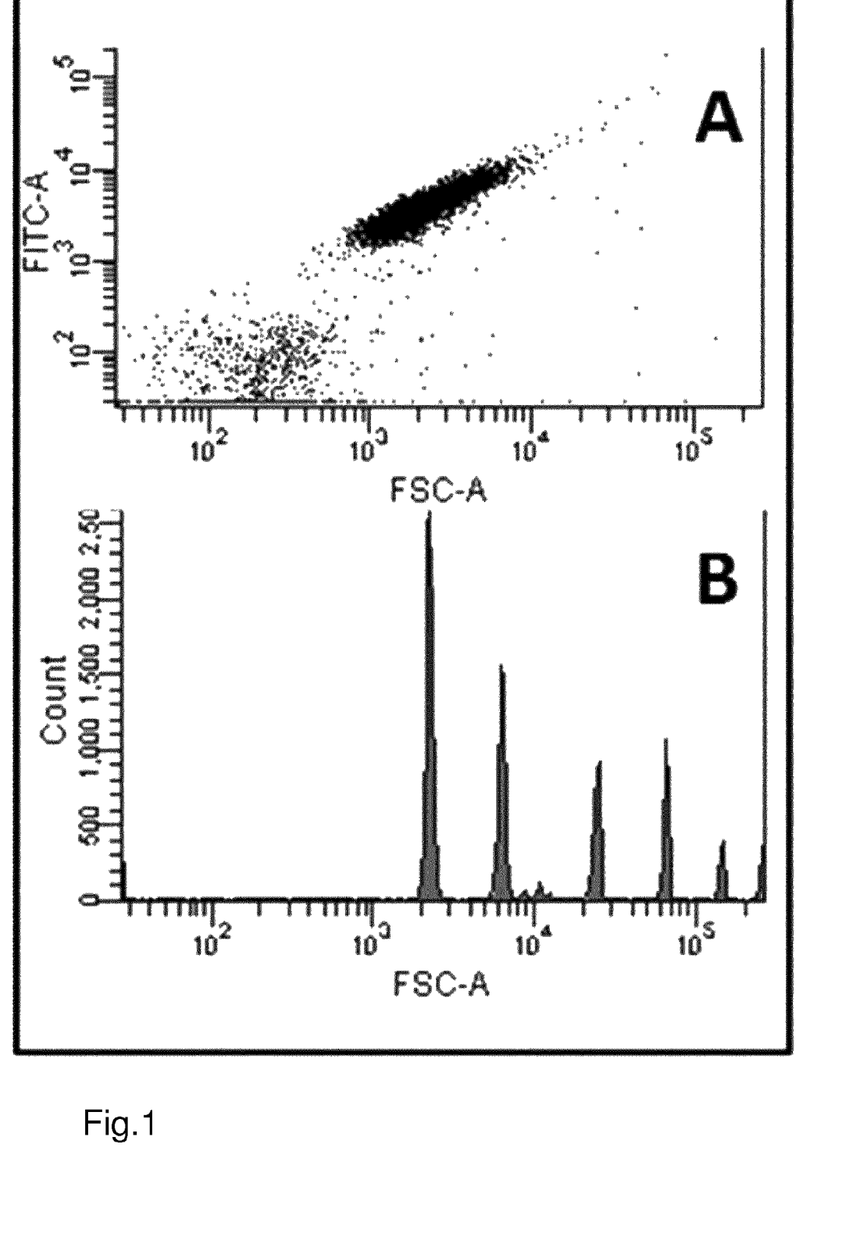
FIG. 1 shows the size determination of Aβ-aggregates using FACS-analysis. Thioflavin T positive Aβ1-42 aggregates can be detected using flow cytometry and are depicted as a homogenous population in the FL1-FITC A (log-scale)- and FSC-A (log-scale) channel in the dot blot (A). The size distribution (defined by FCS-A signal) of Aβ-aggregates was determined using commercially available calibrated size beads (1, 2, 4, 6, 10, and 15 µm) as shown in FSC-A-histogram (B).

According to the present invention, Aβ-aggregates of different Aβ-peptide variants (Aβ1-42, Aβ3-40, and Aβp(E) 3-40), which intercalate with ThT, were generated. These Aβ-aggregates can be detected using FACS-analysis. As described in MM for this purpose seedless soluble Aβ peptides were incubated for 20 h at 37° C. at a concentration of 20 μM. As shown in FIG. 1A (upper panel) a clear homogenous population of ThT positive (measured as FL1 (FITC) positive signals) the FACS assay developed according to the present invention allows the analysis of the in vitro generated Aβ-aggregates. The size distribution of Aβ-aggregates (defined by forward scatter FSC-A) was analyzed using calibrated size beads ranging from 1 to 15 μm (Flow Cytometry Size Calibration Kit (Cat.# F-13838) by Molecular probes) (FIG. 1 lower panel). Using this analysis it was shown that the size of generated Aβ-aggregates ranged as expected from sub-micrometer range up to 10 μm in which most of the generated aggregates range from ~200 nm up to 3 μm.

Reactivity of mAbs with Aβ-Aggregates

Figure 2:
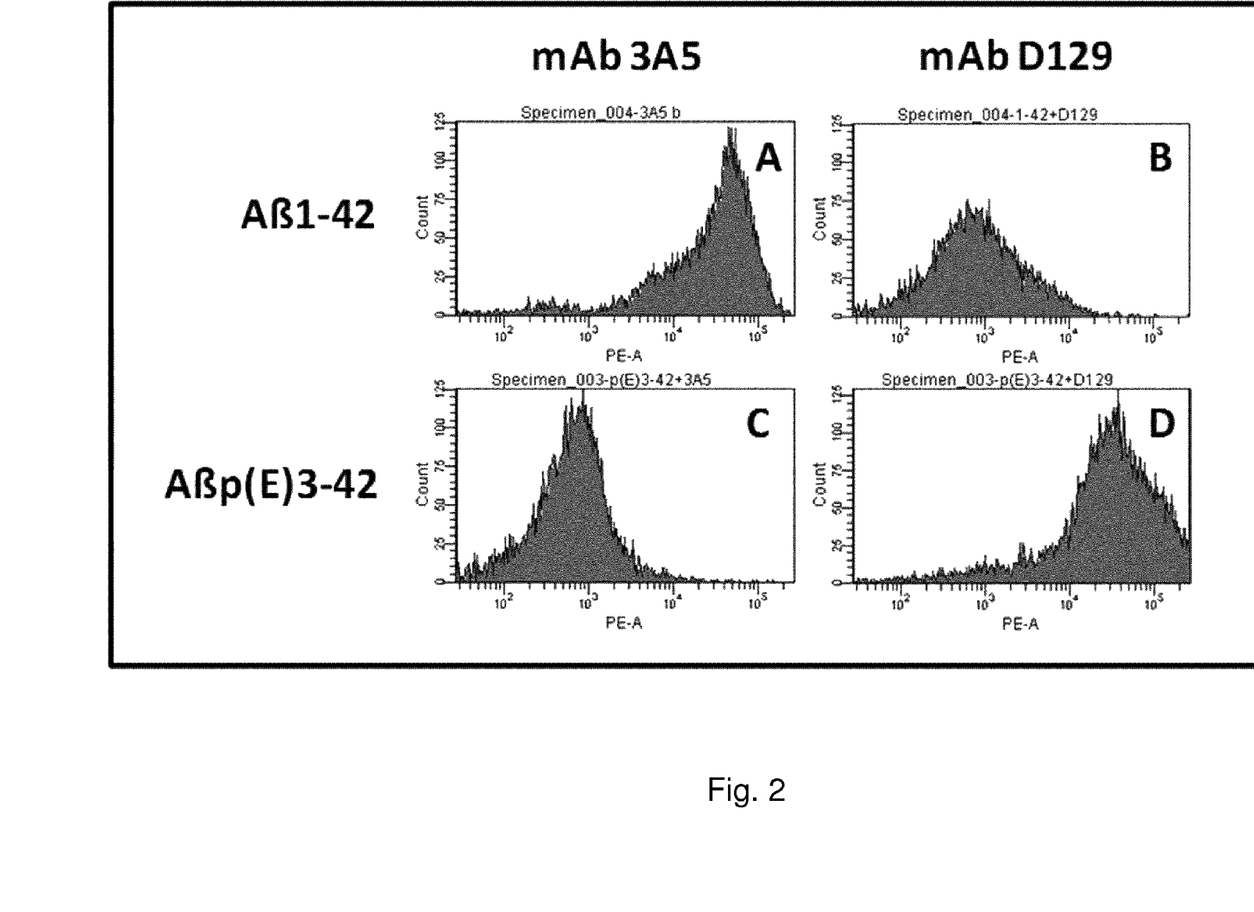
FIG. 2 shows detection of monoclonal antibody reactivity to Aβ-aggregates using FACS-based assay. The Aβ1-42 monoclonal antibody 3A5 binds specifically to Aβ1-42 aggregates (A) but does not interact with Aβp(E)3-42 aggregates (C). In contrast the Aβp(E)3-42 specific antibody D129 binds Aβp(E)3-42 but not Aβ1-42 aggregates (B+D). Reactivity was determined using a secondary anti immunoglobulin-PE-labelled antibody in FL2-PE-channel. Fluorescence intensity as shown in B and C represents background staining as seen when aggregates are incubated with PE-labelled secondary antibody alone.

To define whether Aβ-aggregates allow the binding of Aβ-specific antibodies and to determine whether such an interaction can be monitored using the here described FACS-based assay another set of experiments was undertaken. For this purpose, Aβ1-42 as well as Aβp(E)3-42 aggregates were generated and were incubated with monoclonal antibodies specific either for Aβ1-42 (3A5) or specific for Aβp(E)3-42 (D129). As shown in FACS histograms in FIG. 2, the monoclonal antibody 3A5 binds exclusively Aβ1-42 aggregates whereas mAb D129 interacts only with the N-terminally truncated pyroglutamated Aβ species. This shows that the described FACS-based assay allows the detection of Aβ specific antibodies in a specific manner.

Defining the Sensitivity of Different Detection Methods for Aβ Binding of Human Auto-Antibodies Using IVIG IVIG (intravenous immunoglobulin) is a commercially available blood product. It contains the pooled IgG fraction extracted from plasma derived from healthy donors (human plasma from at least 1000 donors). It has been shown that IVIG preparations contain naturally occurring antibodies (auto-antibodies) specific for Aβ-peptides.

Figure 3:
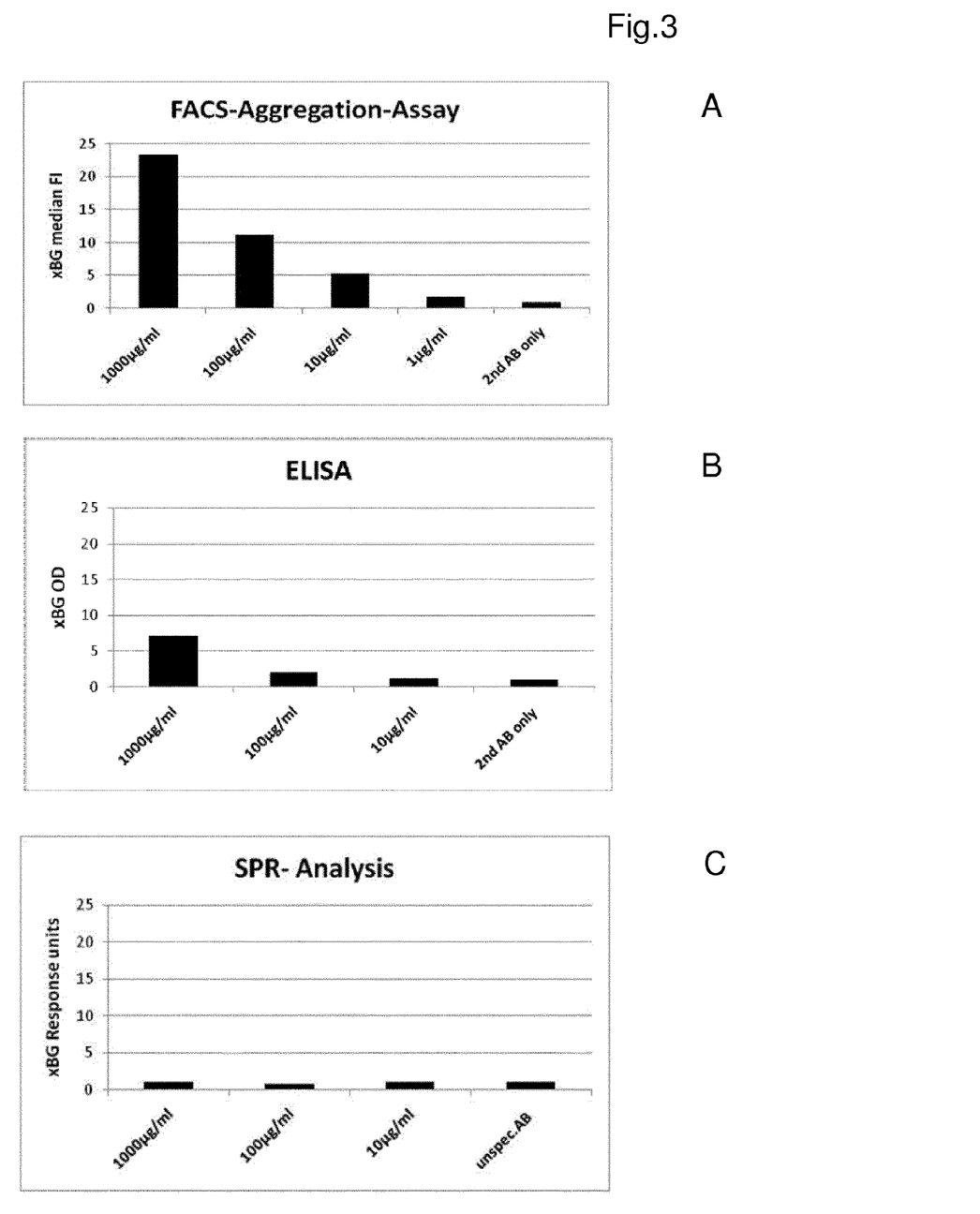

The aim of this experiment was to define and compare the detection limits of three independent detection methods (Biacore, ELISA and the FACS-based assay) for Aβ-reactivity of IVIG (IVIG-Subcuvia, purchased from Baxter, Austria). Aβ1-42 was therefore either immobilized on to the chip surface or onto Maxisorp microtiter plates for SPR or ELISA measurements, respectively. Alternatively, Aβ1-42 aggregates were generated for FACS analysis. Subsequently, different IVIG dilutions were applied to the individual systems and either $R_{max}$ values in case of SPR, OD values in case of ELISA or fluorescence intensity (MFI values) in case of FACS assay were defined. For comparison reasons signal to noise ratio was evaluated for all IVIG concentrations and signals were expressed as fold-background-signal (xBG) (FIG. 3). In case of SPR measurement none of the IVIG concentrations gave a signal above background (FIG. 3C). In contrast to that the control antibody 3A5 gave a strong signal indicating that Aβ1-42 was successfully immobilized to the chip surface and that Aβ-peptides in principle can be recognized on the chip surface by antibodies. Using ELISA as detection method 1000 μg/ml IVIG gave a clear signal above background (7 times BG) whereas the signal induced by 100 μg/ml IVIG was only 2 times background. 10 μg/ml IVIG did not result in a signal greater than background (FIG. 3B). As depicted in FIG. 3A, the FACS-based assay provided signals that were much higher than signals delivered by the other two detection methods. Not only the 1000 μg/ml (24 times BG), or 100 μg/ml (11 fold BG), but also 10 μg/ml (5 fold BG), and 1 μg/ml (almost 2 fold BG) of IVIG dilution resulted in a signal which was clearly above background. This indicates that the newly developed FACS-based assay to detect Aβ-specific auto-antibodies is at least 100 times more sensitive than conventional assays such as ELISA or Biacore.

Defining Anti-Beta Amyloid Antibodies in Human Blood Derived From Healthy Donors and AD Patients a. Reactivity of IgG to Aβ1-42

Figure 4:
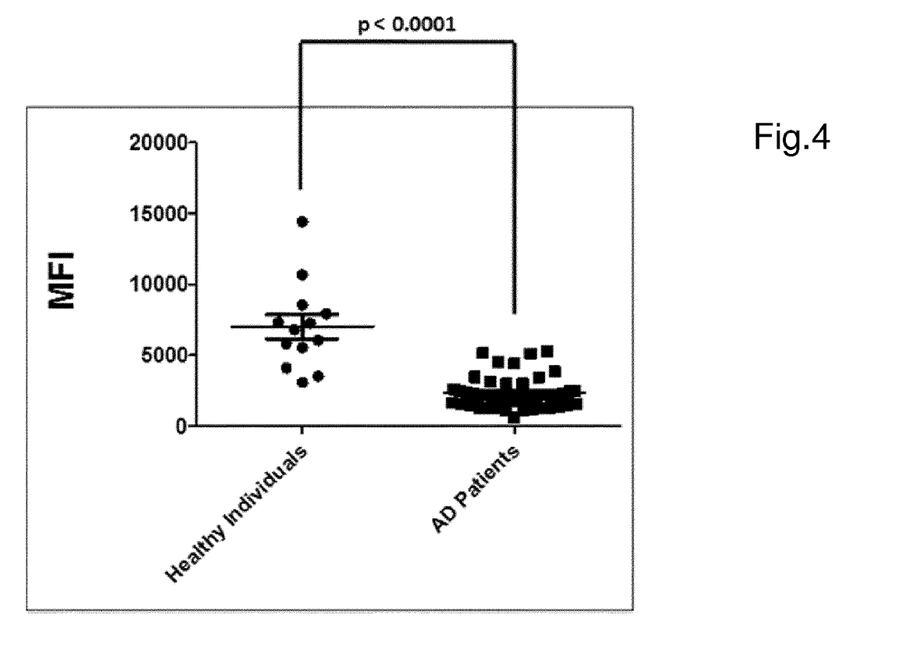

Serum samples derived either from healthy individuals (n=13, ~30 to 50 years old) or AD patients (n=48, ~70 years of age) were analyzed for naturally occurring Aβ-specific antibody con-tent using Aβ-aggregates and FACS analysis as described above. As shown in FIG. 4 naturally occurring antibodies specific for Aβ-aggregates were detected in all samples tested. However, the concentration of such antibodies was significantly lower in blood samples derived from AD patients when compared to serum samples derived from healthy subjects.

Figure 5:
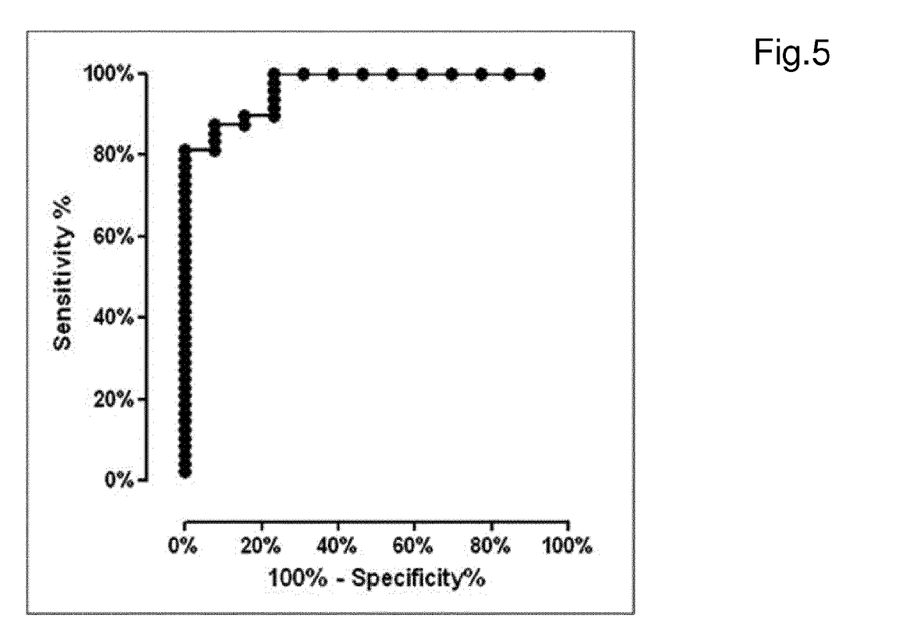

To define the sensitivity and specificity of the present FACS assay to identify persons suffering from AD IgG reactivity to Aβ1-42 aggregates of sera indicated in FIG. 4 were repeated twice and results have been summarized in ROC curves (FIG. 5). This ROC curve analysis showed that specificity was 100% when sensitivity was 81%, and sensitivity was 100% when specificity was 77%, with an area under curve (AUC) of 0.9679.

Figure 6:
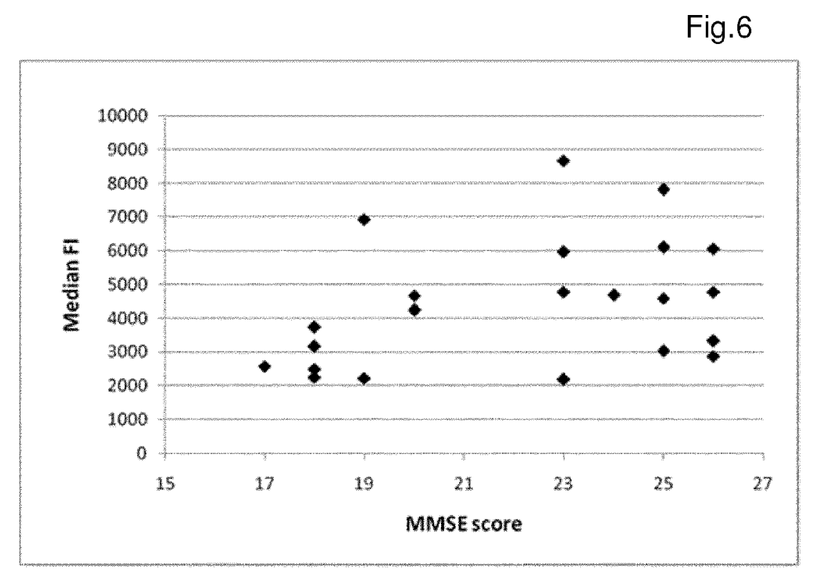
FIG. 6 shows the correlation of IgG reactivity with Mini-Mental State examination (MMSE) scores. 24 AD-patients were examined for MMSE status and sera of those patients were subjected to the described FACS assay and Median FI was determined. A correlation of the collected data is shown in the results and the previous figures.

In an attempt to define a correlation between cognitive and immunologic data the measured IgG reactivity to Aβ-aggregates of AD patient sera (n=24) was correlated with scores from Mini-Mental State examination (MMSE) of the patient's at the time of serum sampling. This correlation revealed that patients with weak test performance show a tendency to reduced IgG reactivity as depicted in FIG. 6. This decrease of Aβ specific IgG reactivity reflects therefore the progression of AD.

In an attempt to define a correlation between cognitive and immunologic data the measured IgG reactivity of AD patient sera (n=24) was correlated with results from Mini-Mental State examination (MMSE). This test is commonly used to screen for cognitive impairment and dementia and estimates the severity of cognitive impairment in an individual at a given point in time. The correlation of MFI with MMSE scores revealed that patients with weak test performance show a tendency to reduced IgG reactivity as depicted in FIG. 6.

b. Reactivity of IgG to Aβ3-42 and Aβp(E)3-42

Figure 7:
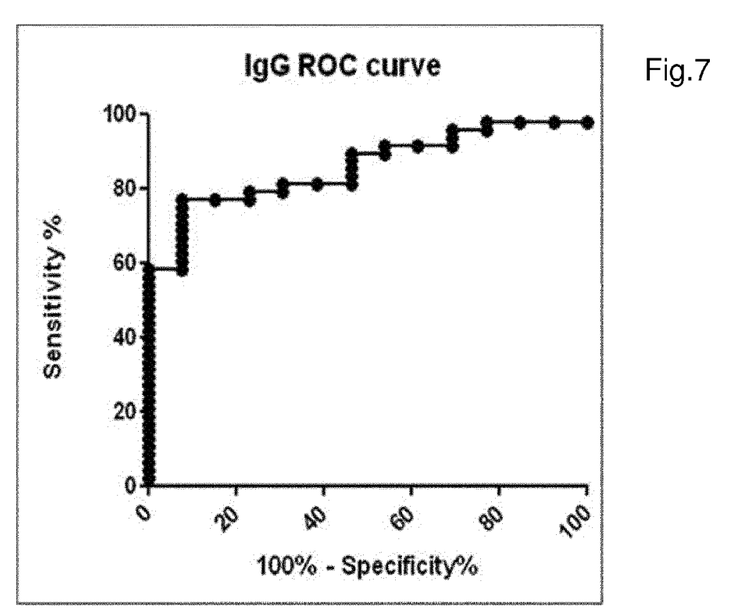
Figure 8:
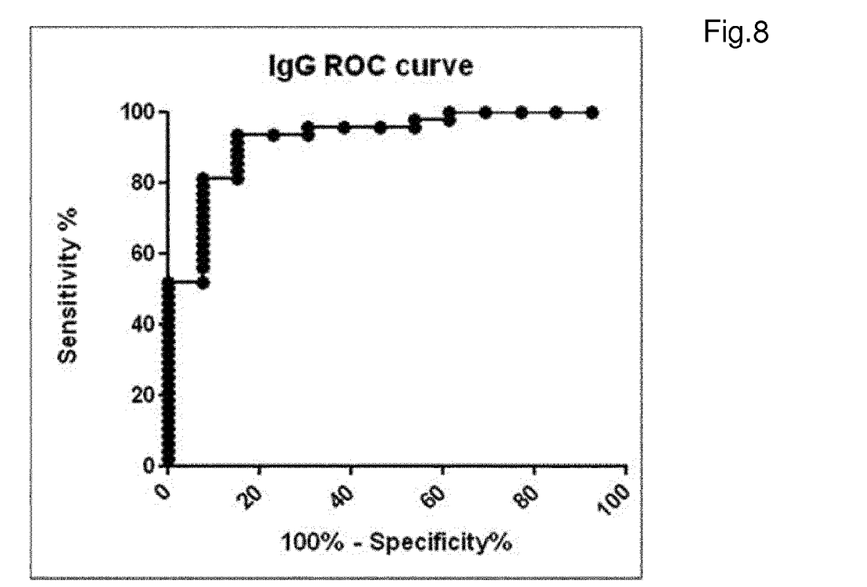

Beside defining reactivity of naturally occurring immunoglobulins in sera of AD patients and healthy subjects to Aβ1-42 aggregates, reactivity of these sera was also defined against Aβ3-42 as well as against Aβp(E)3-42. ROC curves derived from these analyses are depicted in FIG. 7 and FIG. 8. In case of Aβ3-42 (FIG. 7) the ROC curve analysis showed that specificity was 92% when sensitivity was 77%, with an area under curve (AUC) of 0.859.

In case of Aβp(E)3-42 (FIG. 8) the ROC curve analysis showed that specificity was 85% when sensitivity was 93%, with an area under curve (AUC) of 0.928.

c. Reactivity of IgM to Different Aβ-Aggregates

Figure 9A:
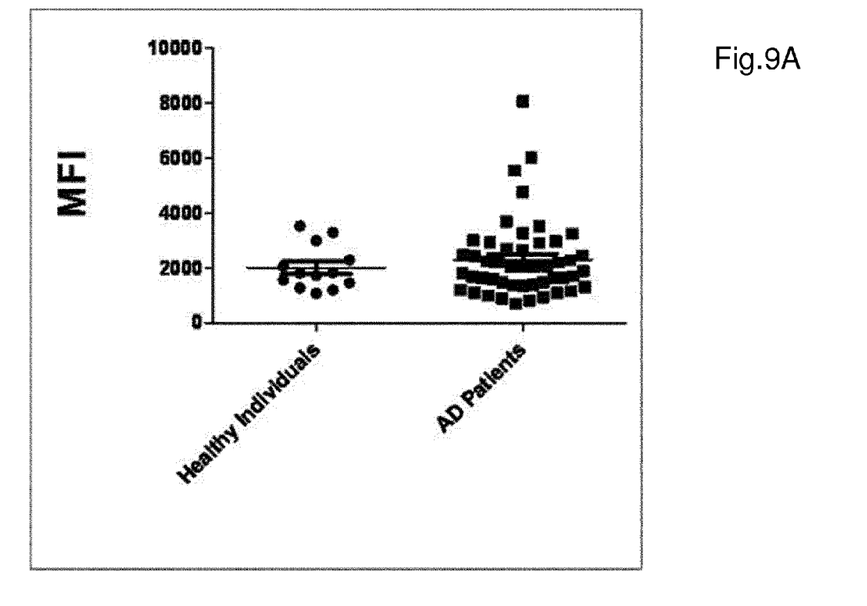
Figure 9B:
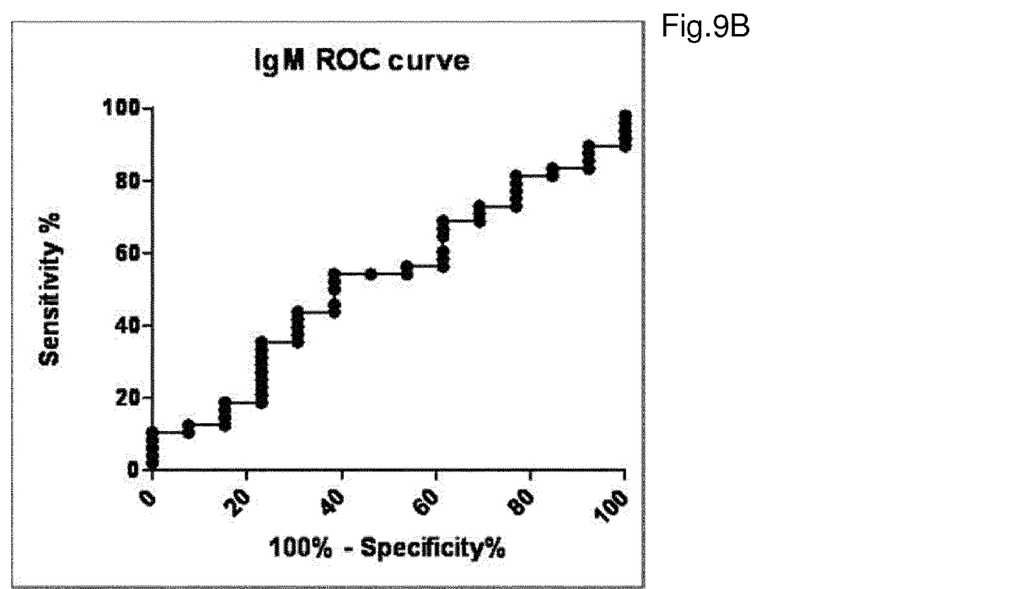

In a next set of experiments Aβ-aggregate specific IgM reactivity was defined in serum samples derived either from healthy individuals or AD patients, using the same sera as described above. As can be seen in FIG. 9A naturally occurring antibodies of IgM isotype specific for Aβ-aggregates were detected in all samples tested. But in contrast to IgG reactivity, serum samples derived from healthy controls do not appear to have higher IgM reactivity to Aβ-aggregates than serum samples derived from AD patients. Therefore, ROC curve analysis did not result in curve depicting sensitivity or specificity (FIG. 9B).

d. Reactivity of IgG and IgM to Aβ-Aggregates after Demasking

Figure 10:
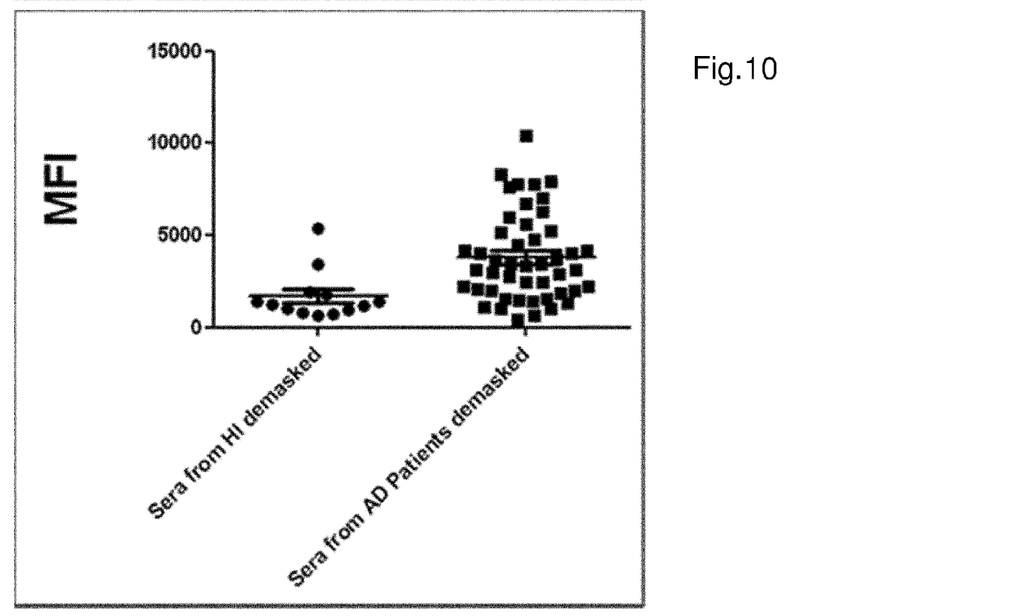
FIG. 10 shows the determination of Aβ-specific IgM auto-antibody reactivity in indicated serum samples after antibody demasking. Control sera from healthy donors (HI), or sera derived from AD-patients were subjected to the described demasking procedure and subsequent FACS assay. Fluorescence intensity of Aβ-aggregates was evaluated in FL2-PE channel and is expressed as Median Fluorescence Intensity (MFI).

In previous studies it has been shown that Aβ-specific auto-antibodies, mainly of the IgM isotype, can be occupied with the Aβ antigen to build an immune complex that is stable and is circulating in the human blood (WO 2010/128139 A1; Marcello et al., 2009; Lindhagen-Persson et al., PLoS ONE 5 (2010): e13928). To define whether Aβ antigens potentially bound to the auto-antibodies may block the reactivity of these antibodies to the in vitro generated Aβ-aggregates, the individual sera were subjected to a demasking procedure as described in material and methods. Using low pH potential immune complexes are disrupted resulting in removal of Aβ antigens from antibody binding domains (antigen dissociation). Thus a demasking procedure could result in higher auto-antibody signals in the FACS based assay if immune complexes are present in serum samples. Interestingly, as depicted in FIG. 10 IgM reactivity of AD patient sera increased significantly after demasking whereas reactivity of healthy control sera did not change compared to untreated sera (compare FIG. 9A). This is in contrast to that what was measured in case of IgG reactivity to Aβ-aggregates. As shown in FIG. 4 sera derived from healthy individuals show higher IgG reactivity to Aβ-aggregates than sera derived from AD patients (in this case sera have not been treated with low pH).

Figure 11:
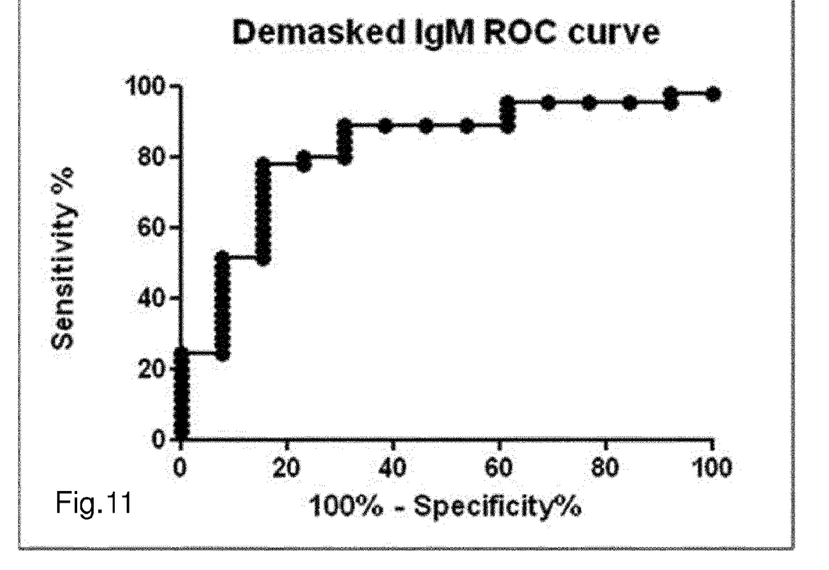
Figure 12:
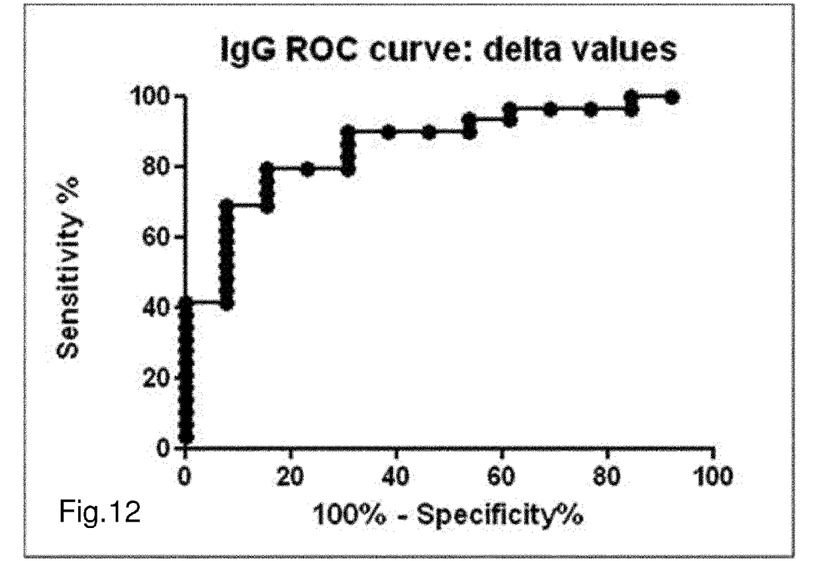

In FIG. 11 results depicted in FIG. 10 have been summarized in ROC curves. This ROC curve analysis showed that specificity was 84% when sensitivity was 78%, with an area under curve (AUC) of 0.822.

To complete this set of experiments a demasking experiment was also performed to detect whether also auto-antibodies of the IgG subtype might be occupied by Aβ antigens. For this purpose all sera were again treated with low pH to disrupt potential immune complexes and subsequently IgG reactivity of sera towards Aβ-aggregates was analyzed. As shown before in the IgM demasking experiment also in this experiment the IgG reactivity towards Aβ-aggregates of sera derived from healthy subjects did not differ between untreated and demasked sera. In contrast to this, sera derived from AD patients showed again a significant increase in Aβ-reactivity after the demasking procedure. Signals derived from binding of serum IgG auto-antibodies to Aβ-aggregates (in this case Aβ1-42) before and after antigen dissociation were compared. The difference between the MFI values derived from the different measurements (untreated vs. demasked) were defined as the dissociation delta (Δ). In FIG. 11 Δvalues of sera derived from healthy controls and Δvalues of sera derived from AD patients are summarized in a ROC curve. As can be seen the Δvalues derived from IgG reactivity can be used as well as parameter to identify AD patients. This ROC curve analysis showed that specificity was 85% when sensitivity was 79%, with an area under curve (AUC) of 0.862.

Conclusions

Based on these results it can be stated that the higher sensitivity of the FACS-aggregation-assay according to the present invention is directly connected to the different aggregation status of Aβ1-42. For BIAcore analysis a freshly dissolved and biotinylated Aβ1-40 was used for immobilization on a streptavidin chip. This method favours the binding of monomeric Aβ1-42 on the chip surface because the peptide is immobilized immediately without preincubation and also the Biotin-tag decelerates the formation of aggregates. Also the coating of Aβ1-42 at pH9 on Maxisorp plates seems to favour the monomeric form of Aβ although the coating of some aggregates cannot be excluded. In these assays the affinities between antibodies and Aβ1-42 peptide are responsible for the limit of detection.

In contrast to these two methods for the FACS-based assay according to the present invention Aβ-1-42 aggregates were specifically induced and used for detection of antibodies specific for Aβ present in IVIG. These bigger molecules offer multiple antibody binding sites. The resulting avidity effect (the sum of multiple synergistic low affine antibody-antigen interactions) can account for the higher sensitivity of this assay and by leading to the detection of low-affine antibodies within the IVIG fraction. Reactivity of IVIG to Aβ-aggregates can also be explained by the existence of an epitope solely present on the aggregated form of Aβ.

The examples clearly show the superiority of the present method over the methods currently available in the field, especially with respect to analytical properties, such as specificity and selectivity.

Clinical Study with a Mimotope Vaccine According to EP 1 583 774 B1 and EP 1 679 319 B1.

An AFFITOPE-vaccine as claimed in EP 1 583 774 B1 and EP 1 679 319 B1 that is able to induce antibodies specifically targeting Aβ-peptides was tested in a clinical study containing two arms. Patients of cohort one were immunized with the AFFITOPE-vaccine containing an adjuvant and patients in cohort two were immunized with the AFFITOPE-vaccine lacking an adjuvant as immune response enhancer. In contrast to the non-adjuvanted vaccine, where an increase of Aβ-specific IgG antibodies cannot be expected, the adjuvanted vaccine should have the capacity to induce antibodies targeting Aβ.

To assess the capacity of the FACS-based assay according to the present invention to monitor induced IgG antibodies over the course of the clinical study sera derived from vaccine recipients were subjected to this assay. One pre-immunization serum (collected before starting the immunization procedure) and 3 post-immunization sera derived from each single patient were analysed. Per time point and patient two individual measurements were done on different aliquots of the serum samples. An increase of Aβ aggregate-specific IgG Abs in individual patients over time would indicate that the FACS assay can be applied to monitor the efficacy of an immunotherapeutic intervention over time and furthermore such results would be indicative for a successful vaccination too.

Applying the FACS-based assay according to the present invention, pre-immunization sera of all study participants were found to contain already Aβ aggregate-specific IgGs as expected. This is in line with recent publications which show that body fluids such as blood (plasma/serum) and CSF contain Aβ aggregate specific IgM and IgG Abs.

Figure 13:
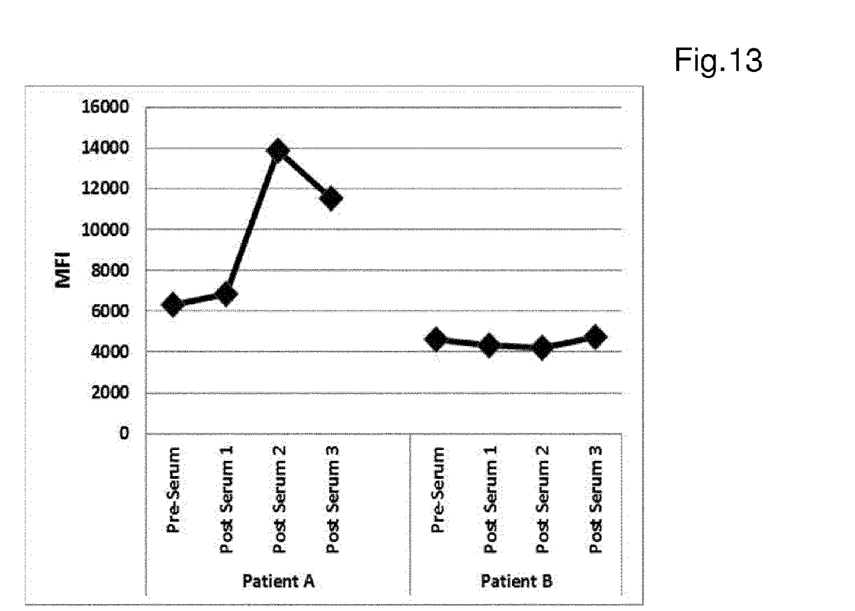
FIG. 13 shows absolute MFI values representing Aβ aggregate-specific IgG antibodies before, during and after vaccinations in patients treated with an AFFITOPE-vaccine. Aβ1-42-reactivity of sera derived from patients immunized with (Patient A) and without ALUM (Patient B) are shown. Fluorescence intensity of Aβ aggregates were evaluated in FL2-PE channel and are expressed as MFI.

Values shown in FIG. 13 depict the mean values of the two measurements over time. In this Figure exemplarily the development of an Aβ-specific IgG antibody response in a patient derived from cohort one (patient A) and a patient immunized with a vaccine lacking the adjuvant (cohort two—patient B) are depicted. As can be seen in FIG. 13 MFI signals of immune sera 2 and 3 from patient A are significantly higher than fluorescence signal derived from pre-serum, indicative for increased Aβ-specific IgGs. In contrast to this, immune sera derived from patient B did not result in increased fluorescence signals. These results are representative for the respective groups.

Figure 14:
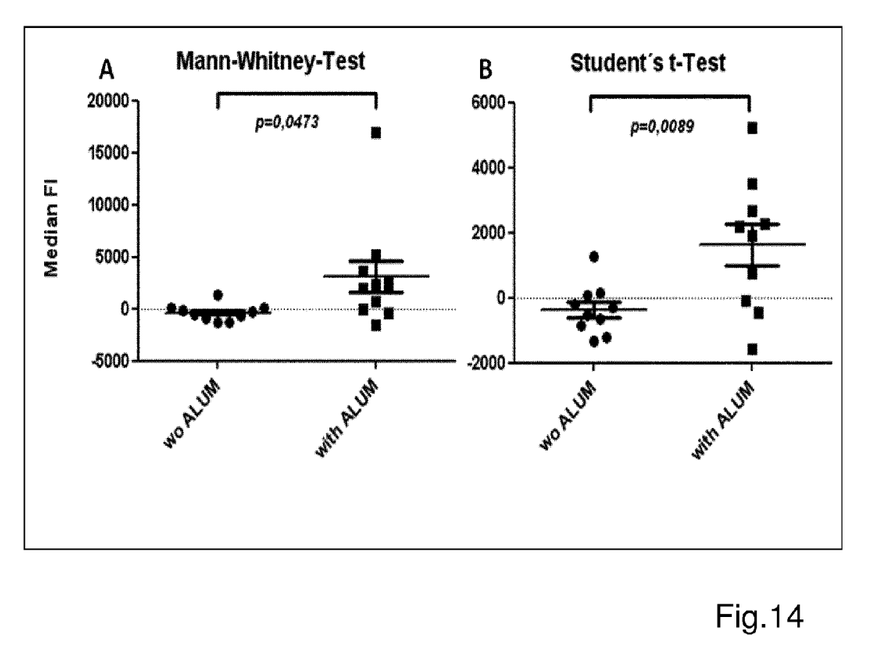
FIG. 14 shows the statistical Analysis of immunoreactivity against Aβ1-42-aggregates expressed in median MFI values from patients immunized with AFFITOPE-vaccine with and without Alum. Due to one extreme in the adjuvanted group a Mann-Whitney-test was performed (non-normal distribution) (A) After removal of the extreme normal distribution was given and a Student's t-test was performed (B) Both test were statistically significant ($p<0.05$).

To define the increase of Aβ1-42-reactivity in individual patients the difference of the mean-MFI-values of the two independent measurements of the last immune serum to the respective pre-sera has been calculated. In FIG. 14 it can be seen that analysis of immune sera using the FACS assay resulted in a clear difference between both groups. Immune sera from patients immunized with adjuvanted vaccine show consistently an increase of Aβ-specific IgGs.

To assess the statistical difference between the median FI-values of patients that received either the adjuvanted or the non-adjuvanted vaccination two different tests were performed. When data of all patients were included there was no normal distribution given between the two groups due to one extreme in the adjuvanted group. Under this precondition a Mann-Whitney-test was performed which resulted in a p-value of 0.0473 (FIG. 14). To make a statistical analysis also under normal distribution conditions the out-layer was removed from the data set and a student's t-test was calculated. This analysis also resulted in a statistical significant p-value of 0.0089 (FIG. 14).

The invention claimed is:

1. A method for diagnosing Alzheimer's disease (AD), wherein Aβ-specific antibodies in a biological sample of a person that is suspected of having AD are detected, the method comprising: contacting the sample with synthetic Aβ-aggregates and allowing the Aβ-specific antibodies to bind to the synthetic Aβ-aggregates, wherein the synthetic Aβ-aggregates are made by incubating Aβ at a pH from 2 to 9 for at least 20 minutes, and have a size of 50 nm to 15 μm, wherein the synthetic Aβaggregates do not comprise beads and the sample is not contacted with beads:
   detecting the Aβ-specific antibodies bound to the synthetic Aβ-aggregates by a single particle detection technique selected from the group consisting of fluorescence-activated cell sorting and mass cytometry; and
   comparing an amount of Aβ-specific antibodies detected with an amount of Aβ-specific antibodies in a sample of known AD status.

2. The method according to claim 1, wherein the Aβ-specific antibodies are human antibodies.

3. The method according to claim 1, wherein the Aβ-specific antibodies are autoantibodies.

4. The method according to claim 1, wherein the synthetic Aβ-aggregates have a size of from 200 nm to 5 μm.

5. The method according to claim 1, wherein the synthetic Aβaggregates are prepared by incubating Aβ-1-42 peptides, Aβ-1-43 peptides, Aβ-3-42, or Aβ-p(E)3-42 peptides at a pH of 2 to 9 for at least 20 min.

6. The method according to claim 1, comprising contacting the sample with the synthetic Aβ-aggregates in an amount of from 0.001 to 1 μM.

7. The method according to claim 1, wherein the biological sample is human blood or a sample derived from human blood, human cerebrospinal fluid or human lymph.

8. The method according to claim 1, wherein the synthetic Aβ-aggregates are contacted with the sample for at least 10 min.

9. The method according to claim 1, further comprising performing demasking on the Aβ-specific antibodies in the sample before contacting the sample with the synthetic Aβ-aggregates.

10. The method according to claim 1, wherein the sample of known AD status is a sample of a patient with AD or a sample of a healthy person.

11. The method according to claim 1, wherein the sample of known AD status is an AD status calibration curve.

12. The method according to claim 1, wherein the detection of an amount of Aβ-specific antibodies in the sample which is lower than a threshold level is indicative of AD, wherein the threshold level is 1500 ng/ml or lower.

13. The method according to claim 1, wherein the detected amount of Aβ-specific antibodies is correlated to a MMSE result of the same person at the same time the sample was taken from the person.

14. The method according to claim 1, wherein the method is performed at least twice on samples of the same person taken at a different time and wherein the detected amounts of Aβ-specific antibodies is correlated to MMSE results of the same person at the same times the samples were taken from the person.

15. The method according to claim 14, wherein the method is performed at least once each six months.

16. The method according to claim 1, wherein the method is suitable for monitoring AD patients.

17. The method according to claim 1, wherein the method is suitable for evaluating a risk of developing AD or for detecting early stage AD.

18. The method according to claim 1, wherein the method is suitable for diagnosis of Parkinson's dementia (PDD), Dementia with Lewy Bodies (DLB), Cerebral Amyloid Angiopathy (CAA), Inclusion body myositis (IBM), or chronic head trauma.

* * * * *